(12) United States Patent
Williams

(10) Patent No.: US 9,958,264 B2
(45) Date of Patent: May 1, 2018

(54) PORTABLE CONTACT ANGLE MEASURING DEVICE

(71) Applicant: Sam Houston State University, Huntsville, TX (US)

(72) Inventor: Darren L. Williams, Huntsville, TX (US)

(73) Assignee: Sam Houston State University, Huntsville, TX (US)

( * ) Notice: Subject to any disclaimer, the term of this patent is extended or adjusted under 35 U.S.C. 154(b) by 0 days. days.

(21) Appl. No.: 15/060,756

(22) Filed: Mar. 4, 2016

(65) Prior Publication Data

US 2016/0258882 A1 Sep. 8, 2016

Related U.S. Application Data

(60) Provisional application No. 62/128,104, filed on Mar. 4, 2015.

(51) Int. Cl.
*G01B 11/22* (2006.01)
*G01B 11/26* (2006.01)
*G01N 13/02* (2006.01)

(52) U.S. Cl.
CPC .......... *G01B 11/26* (2013.01); *G01N 13/02* (2013.01); *G01N 2013/0208* (2013.01)

(58) Field of Classification Search
CPC ............... G01B 11/26; G01N 13/02; G01N 2013/0208; G01N 21/8851; G01N 21/94; G01N 13/00; G01N 2201/0221
USPC .................. 356/627; 348/135, 349
See application file for complete search history.

(56) References Cited

U.S. PATENT DOCUMENTS

| | | | |
|---|---|---|---|
| 3,972,132 A | 8/1976 | Slomski | |
| 4,977,853 A | 12/1990 | Falcoff et al. | |
| 6,088,116 A | 7/2000 | Pfanstiehl | |
| 7,639,862 B2 | 12/2009 | Canning, Jr. et al. | |
| 2004/0012676 A1* | 1/2004 | Weiner | G01N 21/253 348/207.1 |
| 2007/0146702 A1 | 6/2007 | Canning, Jr. et al. | |
| 2008/0018909 A1* | 1/2008 | Osaka | G01B 11/08 356/521 |

(Continued)

OTHER PUBLICATIONS

Williams, D. et al. "Contact Angle Measurements Using Cellphone Cameras to Implement the Bikerman Method" Galvanotechnik Aug. 2011, pp. 1718-1725.

*Primary Examiner* — Sunghee Y Gray
(74) *Attorney, Agent, or Firm* — Meyertons, Hood, Kivlin, Kowert & Goetzel, P.C.; Mark R. DeLuca

(57) ABSTRACT

In some embodiments, a system and/or method may include assessing surface cleanliness. In some embodiments, the system may include a dispensing device. The dispensing device may dispense, during use, a liquid on a surface forming a drop. In some embodiments, the system may include a stage. The stage may support, during use, a digital imaging device above the drop positioned on the surface. In some embodiments, the system may include a light emitter. The light emitter may emit, during use, a beam of light substantially parallel to the surface at the drop. In some embodiments, the system may include an adjustable support coupled to the stage. The adjustable support may adjust, during use, an angle of the stage relative to the surface. In some embodiments, the system is configured to determine a contact angle of the drop relative to the surface.

18 Claims, 2 Drawing Sheets

(56) References Cited

U.S. PATENT DOCUMENTS

| | | | |
|---|---|---|---|
| 2010/0024529 A1* | 2/2010 | Dillingham | G01N 13/02 73/64.52 |
| 2012/0057021 A1* | 3/2012 | Kumagai | G01C 3/08 348/135 |
| 2012/0146247 A1* | 6/2012 | Pomerantz | G06K 19/07732 257/787 |
| 2015/0362417 A1* | 12/2015 | Haberland | G01B 11/26 356/154 |

* cited by examiner

PORTABLE CONTACT ANGLE MEASURING DEVICE

PRIORITY CLAIM

This application claims priority to U.S. Provisional Patent Application No. 62/128,104 entitled "PORTABLE CONTACT ANGLE MEASURING DEVICE" filed on Mar. 4, 2015, which is incorporated by reference herein.

BACKGROUND OF THE INVENTION

1. Field of the Invention

The present disclosure generally relates to assessing surface cleanliness. More particularly, the disclosure generally relates to a portable system and method for measuring a contact angle between a droplet of liquid and a surface.

2. Description of the Relevant Art

There are many instances where a surface must be cleaned sufficiently to permit a following operation to be conducted. For example, a surface that is to be coated (e.g., paint) must first have contaminants (e.g., oil, particulate matter, etc.) removed from the surface so that the coating to be applied will adhere properly to the surface. Proper surface cleanliness is especially important for a smooth metallic surface (e.g., planes, cars, trucks, etc.). Surface irregularities resulting from contamination minimizes coating adhesion through the keying action between the coating film and surface irregularities. Coating adhesion in such cases depends substantially on other adherent mechanisms such as molecular attraction between the metallic surface and the applied coating, and good molecular bonding is achieved only when the surface is properly free of contamination.

The cost of cleaning a surface to be painted increases when the surface being cleaned is part of a large assembled structure. While a surface can be deliberately cleaned beyond the minimum extent necessary for the desired coating adhesion, the expense of such excessive cleaning of the surface is counterproductive.

The measurement of contact angle began in 1805 with the work of Thomas Young. Since then there have been many papers published using contact angle or suggesting new ways to measure contact angle. Almost all of these methods are focused on small samples that may be brought to the lab for analysis in a contact angle measuring device. The field appropriate analyses are mainly the Bikerman method of viewing a drop from above, the Langmuir method of viewing the angle of reflected light from the drop surface, and the drop-shape analysis methods that view the drop from the side. All of these methods have been successfully used in the laboratory. The utility of this method has been revisited recently to show its compatibility and improvement with modern cell phone cameras, macro lenses, and computer spreadsheet programs. But to date, no known source exists that provides the various parts in a self-calibrating contact angle measurement kit that would enable the user to utilize these field-appropriate methods.

SUMMARY

In some embodiments, a system and/or method may include assessing surface cleanliness. In some embodiments, the system may include a dispensing device. The dispensing device may dispense, during use, a liquid on a surface forming a drop. In some embodiments, the system may include a stage. The stage may support, during use, a digital imaging device above the drop positioned on the surface. In some embodiments, the system may include a light emitter. The light emitter may emit, during use, a beam of light substantially parallel to the surface at the drop. In some embodiments, the system may include an adjustable support coupled to the stage. The adjustable support may adjust, during use, an angle of the stage relative to the surface. In some embodiments, the system is configured to determine a contact angle of the drop relative to the surface.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
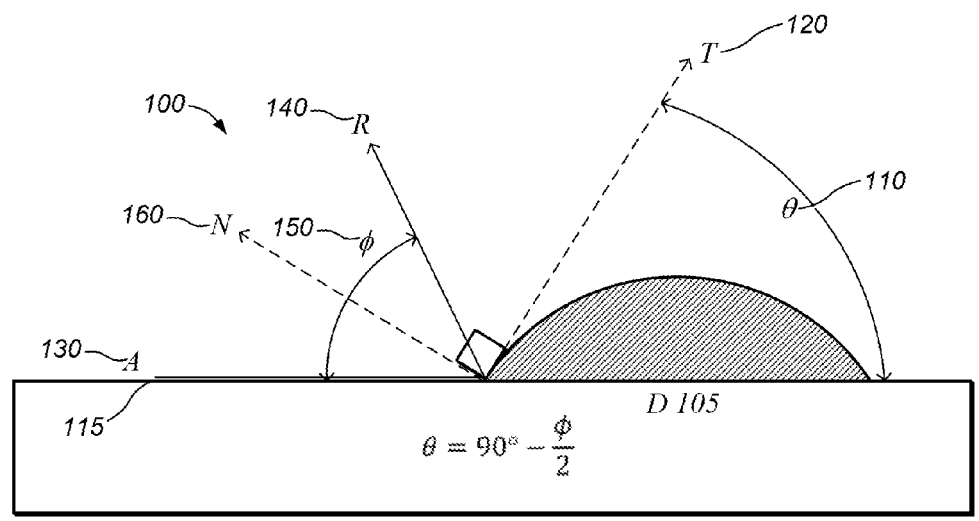
FIG. 1 depicts a perspective view of a representation of an embodiment of a sessile drop showing the definition of contact angle θ.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicate open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

In some embodiments, a system and/or method may include assessing surface cleanliness. In some embodiments, a system may measure a contact angle of a sessile drop. The sessile drop technique is a method used for the characterization of solid surface energies and aspects of liquid surface energies. The main premise of the method is that by placing a droplet of liquid with a known surface energy, specifically the contact angle of the drop, and the known surface energy of the liquid are the parameters which can be used to calculate the surface energy of the solid sample.

This system/method is based upon the Langmuir method of viewing reflected light from the front edge of a sessile drop. FIG. 1 depicts a perspective view of a representation of an embodiment of a sessile drop D 105 showing the definition 100 of contact angle θ 110. The contact angle (e.g., FIG. 1, 110, θ) is defined as the internal angle formed by the plane of the surface 115 and the tangent plane (e.g., FIG. 1, 120, T) of the liquid air interface at the edge of the drop. A light beam traveling close to the surface (e.g., FIG. 1, 130, A) will be reflected up (e.g., FIG. 1, 140, R) at a minimum angle (e.g., FIG. 1, 150, φ). In some embodiments, the light beam may be substantially parallel to the surface. This minimum angle φ may be symmetric about the normal to the surface (e.g., FIG. 1, 160, N). The normal to the surface may be used to define the tangent (e.g., FIG. 1, 120, T). The tangent may be used to compute the contact angle (e.g., FIG. 1, 110, θ). Therefore, the minimum reflection angle φ may be divided by two and subtracted from 90° to compute the contact angle θ. In some embodiments, a contact angle may be determined using EQU. (1).

$$\theta = 90° - (\varphi/2) \qquad (1)$$

Figure 2:
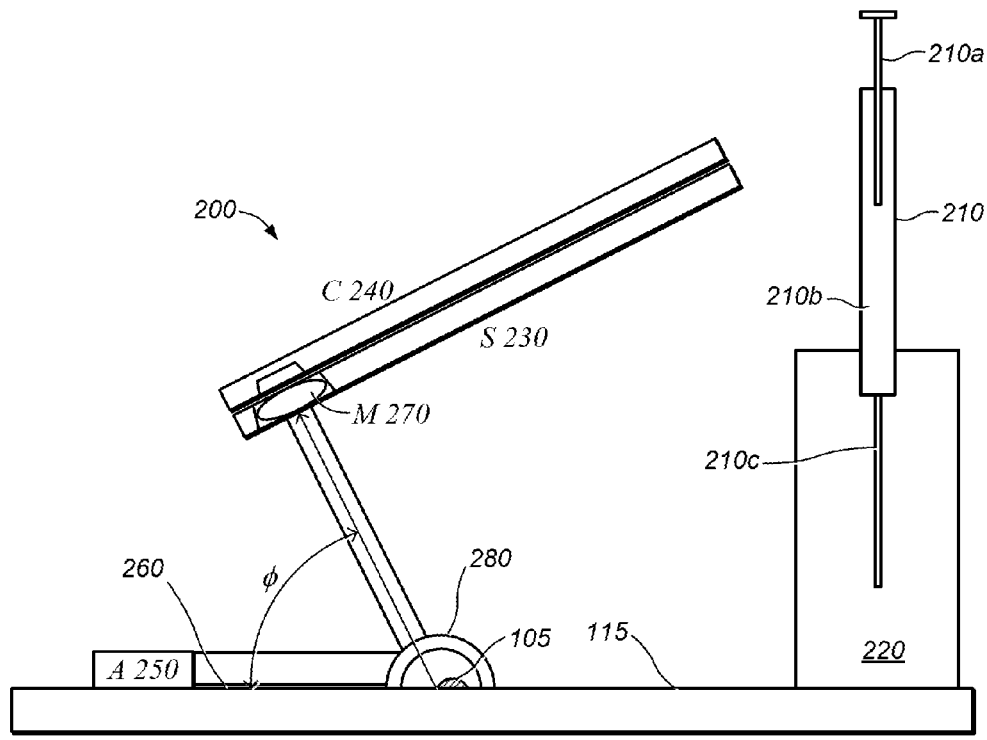
FIG. 2 depicts a side view of a representation of an embodiment of a portable system for assessing surface cleanliness including a dispensing device.

FIG. 2 depicts a side view of a representation of an embodiment of a portable system 200 for assessing surface cleanliness. In some embodiments, the system 200 may include a dispensing device 210. The dispensing device may dispense, during use, an amount of liquid on a surface forming a drop 105. In some embodiment, a particular dispensing device may not be necessary due to the shape and/or volume not being particularly critical to determining the contact angle.

In some embodiments, the drop having a spherical shape may facilitate and/or increase accuracy of the measured contact angle. Whether or not a drop is spherical may be assessed based upon the type of liquid and the volume of the drop. Since most of the contact angle analysis methods are based on the geometry of a perfect sphere, one may use small drops on a level planar surface, although non-level and curved surfaces have been addressed. According to Extrand and Moon based on Equation (2), a 10 µL water droplet will be spherical if it adopts a shape with a contact angle between 10° and 140°. Equation (2) describes the maximum spherical volume ($V_{max}$ in µL) in general terms suitable for any liquid where g is the acceleration due to gravity (9.81 m/s$^2$), γ is the liquid surface tension in mN/m, and ρ is the liquid density in g/cm$^3$.

$$V_{max} = \frac{\pi}{48}\left(\frac{\gamma}{\rho g}\right)^{3/2} \tan(\theta/2)(3 + (\tan(\theta/2))^2)\left[\left(1 + 8\frac{(\sin\theta)^2}{1 - \cos\theta}\right)^{1/2} - 1\right]^3 \qquad (2)$$

In some embodiments, the amount of liquid may include a measured amount of liquid. In some embodiments, the dispensing device may include an accurate device. In some embodiments, the dispensing device may include a pump.

In some embodiments, the dispensing device 210 may include a syringe. A syringe may include a simple pump consisting of a plunger 210a that fits tightly in a tube 210b. The plunger may be pulled and pushed along an inside of a cylindrical tube, allowing the syringe to take in and expel fluids through an orifice at the open end of the tube. The open end of the syringe may be fitted with a hypodermic needle 210c, a nozzle, or tubing to help direct the flow into and out of the barrel.

In some embodiments, the dispensing device may include a stand 220. The stand may function to stabilize the dispensing device during use. The stand may allow a user to more accurately dispense a droplet onto a surface.

In some embodiments, the dispensing device may have a relative uncertainty of less than 5%. In some embodiments, the dispensing device may have a relative uncertainty of less than 2%. Relative uncertainty is calculated as the standard deviation divided by the mean value. This is also known as the relative standard deviation (RSD) in percent. Others call this the coefficient of variation (CV).

In some embodiments, the system 200 may include a stage S 230. The stage may support, during use, a digital imaging device C 240. In some embodiments, the stage is coupled to the digital imaging device. In some embodiments, the system may include a light emitter A 250. The light emitter may emit, during use, light along the surface at the drop 105. The light emitter may emit a beam of light 260. The light emitter may emit, during use, a beam of light substantially parallel to the surface at the drop. The light emitter may be coupled to the stage. In some embodiments, the light emitter may emit a coherent beam of light (e.g., a laser pointer). In some embodiments, the light source may simply emit a beam of light (e.g., a pin hole light source).

In some embodiments, the light source sends a beam of light along the surface toward the edge of the drop (e.g., as depicted in FIG. 2). This beam of light may be reflected upward by the drop. A digital imaging device with tilt-sensing capability may be mounted on an adjustable stage. The stage 230 may be coupled to a base 280 (e.g., as depicted in FIG. 2). The stage may be adjustable relative to the base. The stage may rotate (e.g., using a hinged joint, ball joint, etc.) through an arc relative to the base. In some embodiments, the stage may move relative to the base using a powered (e.g., electrical) motor, for example, in a substantially automated fashion. The stage may be tilted until the digital imaging device measures the smallest value of the reflection angle ($\varphi$) that reflects the point-source of light. The digital imaging device stage may be equipped with a macro lens that improves the ability of the digital imaging device to capture a close-up photo of the drop at the minimum reflection angle $\varphi$.

Figure 3:
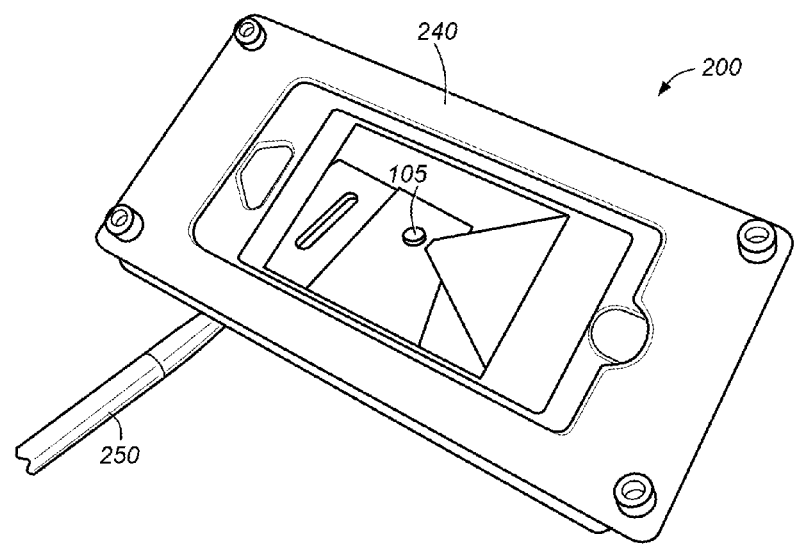
FIG. 3 depicts a perspective view of a representation of an embodiment of a portable system for assessing surface cleanliness.
Figure 4:
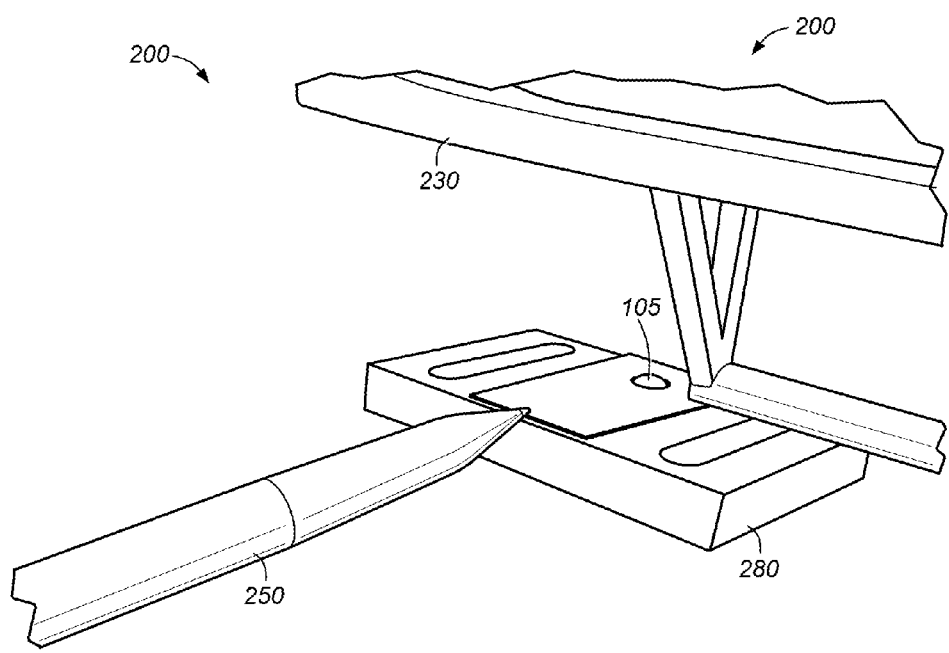
FIG. 4 depicts a side perspective view of a representation of an embodiment of a portable system for assessing surface cleanliness.

In some embodiments, the system is configured to assess a contact angle of the drop with the surface 115. FIGS. 3-4 depict perspective views of a representation of an embodiment of a portable system 200 for assessing surface cleanliness. In some embodiments, a distance between the stage and the calibration feature is determined by a focal length of the digital imaging device. This allows the drop and the calibration feature to be in focus. In some embodiments, a distance between the stage and the calibration feature is adjustable and determined by a focal length of the digital imaging device. A system for adjusting the distance may include systems which allow for incremental adjustment of the distance. In some embodiments, the system for distance adjustment may include threaded elongated members coupling the stage to the calibration feature. In some embodiments, the system for distance adjustment may include a ratcheting system coupling the stage to the calibration feature.

In some embodiments, the digital imaging device comprises a lens. The lens may include a macro or similar lens. A macro lens may allow the digital imaging device to focus on the drop and/or calibration feature.

In some embodiments, the stage includes a lens M 270 (e.g., as depicted in FIG. 2) incorporated into the stage. The lens in the stage may function in combination with the digital imaging device. A distance between the stage and the calibration feature is determined by a focal length of the macro lens. In some embodiments, the stage includes the digital imaging device such that the stage and digital imaging device are one unit.

In some embodiments, the digital imaging device may include a digital camera. The digital imaging device may include an electronic device which includes a digital camera (e.g., cellular phones, tablets, etc.).

In some embodiments, the digital imaging device may include some type of relative orientation device allowing for the determination of $\varphi$. In some embodiments, the digital imaging device may include a tilt sensor. A tilt sensor may determine tilting in often two axes of a reference plane in two axes. In contrast, a full motion would use at least three axes and often additional sensors. In some embodiments, a tilt sensor may determine tilting in at least three axes. One way to measure tilt angle with reference to the earths ground plane, is to use an accelerometer. Typical applications can be found in the industry and in game controllers.

In some embodiments, the digital imaging device may include a proportional tilt sensor. In these sensors, the output is proportional to the degree of tilt. Proportional tilt sensors are also of various types depending on the tilt mechanism used. Proportional tilt sensors may include electrolytic tilt sensors, MEMS based sensor, or optical tilt sensors.

In some embodiments, a software program or application may assess the contact angle. Software may assess the angle $\varphi$. In some embodiments, as a relative angle of the digital imaging device relative to the surface is adjusted software may automatically determine a minimum angle of the light beam reflected up (e.g., FIG. 1, $\varphi$). In some embodiments, software may be used in combination with a powered (and possibly automated) adjustment mechanism such that a contact angle may be substantially automatically assessed.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A portable system, comprising:
   a portable stage which supports, during use, a digital imaging device above a drop positioned on a surface;
   a light emitter which emits, during use, a beam of light substantially parallel to the surface at the drop; and
   an adjustable support coupled to the stage which adjusts, during use, an angle of the stage relative to the surface;

wherein the system determines a contact angle of the drop relative to the surface for assessing surface cleanliness and/or surface energy.

2. The system of claim 1, further comprising a dispensing device which dispenses, during use, a measured amount of liquid on a surface forming a drop.

3. The system of claim 1, further comprising a securing system for inhibiting movement of the digital imaging device relative to the portable stage.

4. The system of claim 1, further comprising a digital imaging device comprising a tilt sensor.

5. The system of claim 1, further comprising a digital imaging device comprising a sensor configured to at least detect orientation of the digital imaging device relative to the surface.

6. The system of claim 1, wherein the light emitter comprises emits a coherent beam of light.

7. The system of claim 1, wherein the stage comprises the digital imaging device.

8. The system of claim 1, wherein a distance between the stage and the surface is adjustable and determined by a focal length of the digital imaging device.

9. The system of claim 1, wherein the stage comprises a macro lens.

10. The system of claim 1, wherein the stage comprises a macro lens, and wherein a distance between the stage and the surface is determined by a focal length of the macro lens.

11. The system of claim 1, wherein the digital imaging device comprises a multi-function device.

12. A method comprising:
supporting a digital imaging device using an adjustable stage;
emitting a beam of light substantially parallel to a surface at a drop positioned on the surface using a light emitter; and
adjusting an angle of the digital imaging device relative to the drop using the adjustable stage until the digital imaging device measures a minimum value of a reflection angle of the beam of light off of the drop;
determining a contact angle of the drop relative to the surface; and
assessing surface cleanliness and/or surface energy.

13. The method of claim 12, further comprising dispensing a liquid on a surface forming a drop using a dispensing device.

14. The method of claim 12, further comprising dispensing a measured amount of liquid on a surface forming a drop using a dispensing device.

15. The method of claim 12, determining a distance between the stage and the surface using a focal length of the digital imaging device.

16. The method of claim 12, adjusting a distance between the stage and the surface using a focal length of the digital imaging device.

17. The method of claim 12, wherein the stage comprises a macro lens.

18. The method of claim 12, wherein the stage comprises the digital imaging device.

* * * * *